US010299973B2

(12) United States Patent
Conte

(10) Patent No.: US 10,299,973 B2
(45) Date of Patent: May 28, 2019

(54) MOTORIZED WHEELCHAIR FOR DISABLED OR ELDERLY USERS

(71) Applicant: Giovanni Conte, Paderno Dugnano (IT)

(72) Inventor: Giovanni Conte, Paderno Dugnano (IT)

( * ) Notice: Subject to any disclaimer, the term of this patent is extended or adjusted under 35 U.S.C. 154(b) by 0 days.

(21) Appl. No.: 15/813,869

(22) Filed: Nov. 15, 2017

(65) Prior Publication Data

US 2018/0147100 A1    May 31, 2018

(30) Foreign Application Priority Data

Nov. 28, 2016    (IT) .......................... 102016000120097

(51) Int. Cl.
| | | |
|---|---|---|
| *B62K 23/02* | (2006.01) | |
| *B62K 23/06* | (2006.01) | |
| *A61G 5/04* | (2013.01) | |
| *A61G 5/10* | (2006.01) | |
| *A61F 4/00* | (2006.01) | |
| *A61G 5/02* | (2006.01) | |

(52) U.S. Cl.
CPC .................. *A61G 5/04* (2013.01); *A61F 4/00* (2013.01); *A61G 5/047* (2013.01); *A61G 5/10* (2013.01); *A61G 5/1008* (2013.01); *A61G 5/1035* (2013.01); *B62K 23/02* (2013.01); *B62K 23/06* (2013.01); *A61G 5/022* (2013.01); *A61G 5/025* (2013.01); *A61G 5/1013* (2013.01); *A61G 2203/10* (2013.01)

(58) Field of Classification Search
CPC ........... Y10T 74/2044; Y10T 74/20012; Y10T 74/2107; Y10T 477/89; Y10T 477/6808; B60W 10/08; B60W 10/184; F16D 65/14; F16D 65/28; B64D 31/04; B63H 21/213; B62K 23/02; B62K 23/06; B62M 25/04
See application file for complete search history.

(56) References Cited

U.S. PATENT DOCUMENTS

| | | | | |
|---|---|---|---|---|
| 2,071,063 | A * | 2/1937 | De Florez | B64D 31/04 188/106 R |
| 2,787,353 | A * | 4/1957 | Spraragen | F16B 1/04 192/223.2 |
| 3,057,221 | A * | 10/1962 | Smith | B63H 21/213 477/113 |
| 3,117,648 | A * | 1/1964 | Landreth | B60K 1/00 180/210 |
| 4,049,097 | A * | 9/1977 | Pratt | F16B 21/02 192/223.2 |
| 5,134,897 | A * | 8/1992 | Romano | B62K 23/04 74/473.13 |

(Continued)

FOREIGN PATENT DOCUMENTS

| | | |
|---|---|---|
| CN | 205601612 U | 9/2016 |
| WO | 2007/049301 A2 | 5/2007 |

*Primary Examiner* — Joseph M Rocca
*Assistant Examiner* — Daniel S Yeagley
(74) *Attorney, Agent, or Firm* — Egbert Law Offices, PLLC

(57) ABSTRACT

A motorized wheelchair for disabled or elderly users has a frame, a seat for the disabled driver, a handlebar, a motor provided with an acceleration apparatus, a wheel assembly and a braking apparatus of the wheels. The wheelchair has a dual-action control device that is capable of being interfaced with the acceleration apparatus of the motor and with the braking apparatus of the wheels.

8 Claims, 5 Drawing Sheets

(56) References Cited

U.S. PATENT DOCUMENTS

| | | | | |
|---|---|---|---|---|
| 5,287,766 | A * | 2/1994 | Nagano | B62K 23/06 74/502.2 |
| 5,423,277 | A * | 6/1995 | Gai | B63H 21/213 114/144 R |
| 5,651,422 | A * | 7/1997 | Casali | A61G 5/047 180/13 |
| 6,142,281 | A * | 11/2000 | Campagnolo | B62K 23/06 192/217 |
| 6,595,894 | B2 * | 7/2003 | Hanatani | B62K 23/04 475/349 |
| 7,216,728 | B2 * | 5/2007 | Huang | A61G 5/047 180/13 |
| 7,571,788 | B2 * | 8/2009 | Barnard | F02D 11/04 180/332 |
| 7,905,158 | B2 * | 3/2011 | Dal Pra | B62K 23/06 74/473.14 |
| 7,938,039 | B2 * | 5/2011 | Cox | F16C 1/18 74/501.6 |
| 8,096,208 | B2 * | 1/2012 | Sean | B62K 23/06 74/498 |
| 8,584,549 | B2 * | 11/2013 | Cheng | G05G 11/00 74/482 |
| 8,684,113 | B1 * | 4/2014 | Laconis | A61G 5/047 180/11 |
| 9,872,805 | B2 * | 1/2018 | Bach Castillo | B62K 5/025 |
| 2004/0060381 | A1 * | 4/2004 | Gavillucci | F16H 59/042 74/473.3 |
| 2008/0073197 | A1 * | 3/2008 | Saito | B62H 1/02 200/564 |
| 2010/0025124 | A1 | 2/2010 | Arpino | |
| 2013/0220057 | A1 * | 8/2013 | Kawakami | B62M 25/04 74/501.6 |

\* cited by examiner

MOTORIZED WHEELCHAIR FOR DISABLED OR ELDERLY USERS

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to a motorized wheelchair for disabled or elderly users of improved type, which is provided with a dual-action control device capable of being interfaced with the acceleration apparatus of the motor and with the braking apparatus of the wheels of the wheelchair.

2. Description of Related Art Including Information Disclosed Under 37 CFR 1.97 and 37 CFR 1.98

As it is known, the motorized wheelchairs for disabled or elderly users who have lost their motor capacities and are not able to stand on their legs, in spite of having maintained the use of their hands, are provided with a traditional handlebar whereon two separate controls are disposed, respectively for the accelerator and the brake, suitable for being actuated each one with one hand.

The accelerator control usually consists in a knob or in a thumb-operated control, whereas the brake control usually consists in a knob associated with a lever that must be grabbed and pulled by the user's fingers, while keeping the thumb and the palm of the hand on the knob of the brake.

Evidently, a wheelchair provided with two separate controls for the accelerator and the brake is designed for users without problems of joint mobility or force in their hands or fingers, which are especially needed to actuate the brake lever.

The purpose of the present invention is to provide a motorized wheelchair for disabled or elderly users of improved type that can be also controlled by users affected by tetraplegia, tetraparesis, arthrosis or other pathologies that impair the correct use of one hand. As a matter of fact, in such a case, the user cannot operate two separate controls with one hand because the controls are disposed one far from the other on the handlebar and are operated with a different maneuver.

The motorized wheelchair of the invention has been devised to solve the problems caused by the specific disability of users who can only use one hand or have a reduced mobility of both hands.

In particular, the main purpose of the present invention is to make it possible to control with only one hand a motorized wheelchair designed for users capable of operating the accelerator and the brake controls with two hands, respectively.

An additional purpose of the present invention is to make it possible to control with only one hand, either the left or the right hand, a motorized wheelchair designed for users capable of operating the accelerator and the brake controls with two hands, respectively.

These and other advantages have been achieved by the improved motorized wheelchair according to the present invention, the main and secondary characteristics of which are disclosed in the claims attached to this description.

BRIEF SUMMARY OF THE INVENTION

The improved motorized wheelchair according to the invention comprises a dual-action control device that is capable of being interfaced with the acceleration apparatus of the motor and with the braking apparatus of the wheels of the wheelchair.

The control can be operated with one hand with a push-pull movement and does not require a special force or ability of the fingers and the wrist (like, for example, for operating a lever brake).

More precisely, said dual-action control device comprises only one maneuvering lever that can oscillate both in clockwise and in anticlockwise direction, starting from an idle position in which said maneuvering lever is operatively ineffective both in terms of braking action and accelerating action.

Said maneuvering lever is associated with a first annular disc that is interfaced and cooperates with a second annular disc, in such a way that said second annular disc is driven into rotation by the first annular disc only in one of the two directions of rotations of the maneuvering lever.

The operation cable of the braking apparatus of the wheels of the wheelchair is fastened to the second annular disc, whereas the maneuvering lever is coupled with the actuation means of the acceleration apparatus of the motor of the wheelchair. In view of the above, when the maneuvering lever is pushed by the user in the direction of rotation that enables the braking apparatus, the acceleration apparatus does not receive any actuation command, and vice versa.

BRIEF DESCRIPTION OF THE SEVERAL VIEWS OF THE DRAWINGS

For the sake of clarity, the description of the invention continues with reference to the enclosed drawings, which refer to a preferred embodiment and therefore have a merely illustrative, not limiting value, wherein.

DETAILED DESCRIPTION OF THE INVENTION

Figure 1:
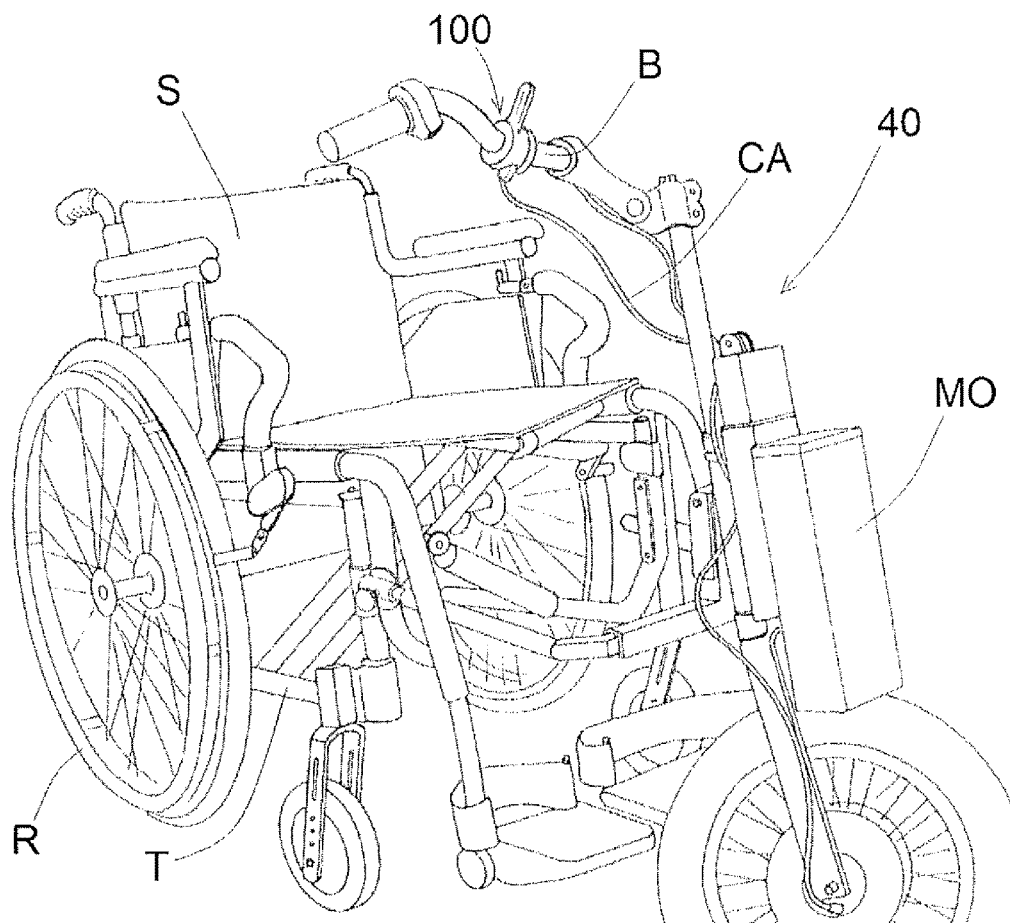
FIG. 1 is a perspective view of the wheelchair according to the invention.

With reference to FIG. 1, the motorized wheelchair for disabled or elderly users (CA) according to the invention is of the type that traditionally comprises a frame (T), a seat (S) for the disabled driver, a handlebar (B), a motor (MO) provided with acceleration apparatus, a wheel assembly (R) and a braking apparatus (F) of said wheels (R).

Said wheelchair (CA) is provided with a dual-action control device (100) suitable for being interfaced with the acceleration apparatus of the motor (MO) and with the braking apparatus (F) of the wheels (R).

Said dual-action control device (100) comprises a shell-shaped housing (1) provided with a cylindrical internal chamber (1*a*) closed by a cap (2).

Figure 3:
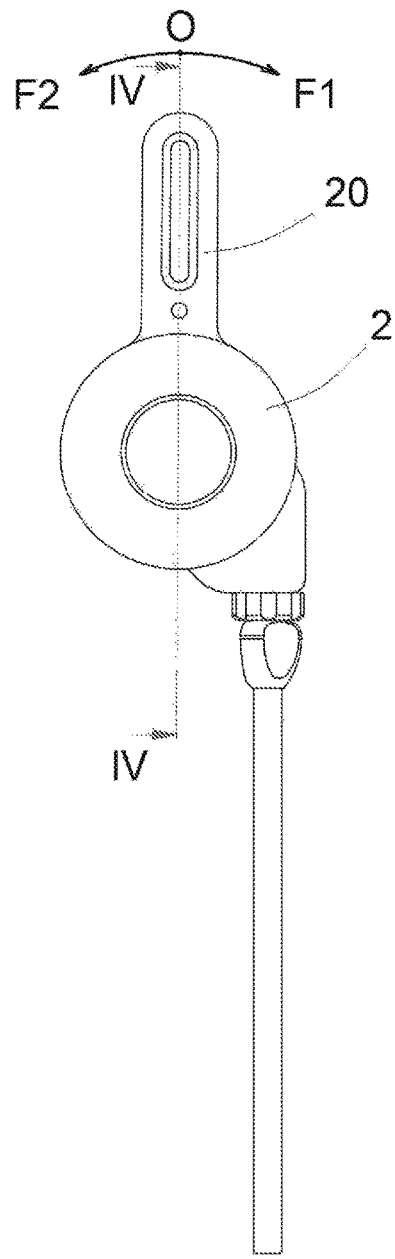
FIG. 3 is the side view of the bivalent control device of FIG. 2.

Said dual-action control device (100) also comprises a maneuvering lever (20) capable of oscillating from an idle position indicated with letter "O" in FIG. 3 both in clockwise direction (indicated by the arrow F1 in FIG. 3) and in anticlockwise direction (indicated by the arrow F2 in FIG. 3) relative to the longitudinal axis (X) of said cylindrical chamber (1*a*) obtained inside the shell-shaped housing (1).

Said maneuvering lever (20) is associated with a first annular disc (21) that has its center on the axis (X); more precisely, said maneuvering lever (20) consists in an arm that radially protrudes from the external edge of said annular disc (21) for such a length that its distal section (20*a*) is disposed outside of said housing (1).

Said first annular disc (21) is interfaced and cooperates with a second annular disc (30) housed inside said chamber (1*a*), which likewise has its center on the axis (X); a coupler is provided between the first annular disc (21) and the second annular disc (30) in such a way that said second annular disc (30) is driven into rotation by the first annular disc (21) only in one of the two directions of rotation of the maneuvering lever (20).

Figure 2:
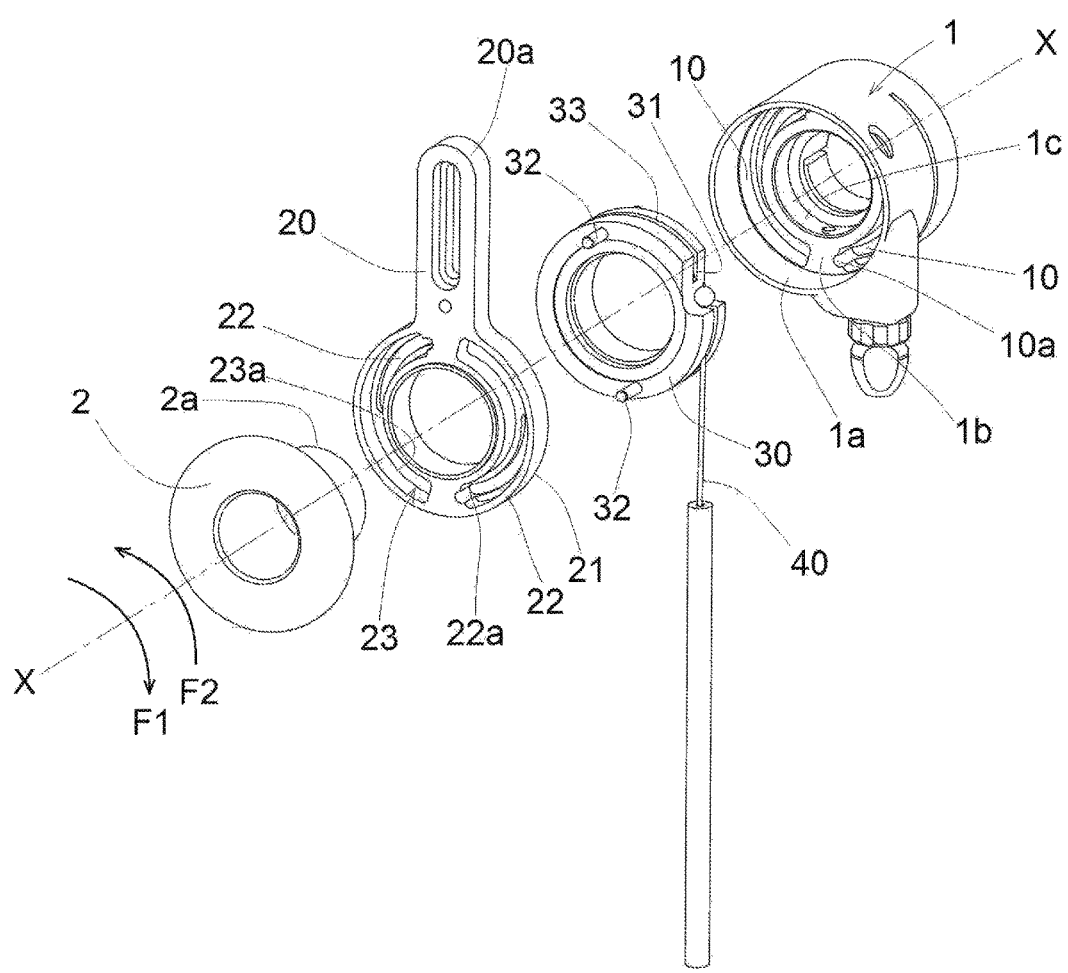
FIG. 2 is an exploded view of the bivalent control device seen from a first angle.

With reference to FIG. 2, the second annular disc (30) is driven into rotation by the first annular disc (21) only when the maneuvering lever (20) is pushed in the anticlockwise direction indicated by the arrow (F2).

The coupler between the first annular disc (21) and the second annular disc (30) comprises:
a diametrally opposite pair of identical curved slots (22) obtained on the first annular disc (21);
a diametrally opposite pair of identical cylindrical pegs (32) obtained on the second annular disc (30) on the side facing the first annular disc (21), having an axis parallel to the axis (X) and suitable dimensions to be slidingly inserted in said curved slots (22).

The parts of the device (100) are mounted in such a way that when the maneuvering lever (20) is in idle position, the pegs (32) are disposed inside said curved slots (22) in such a way to receive the driving thrust from one (22*a*) of the ends of said curved slots (22) as soon as the maneuvering lever (20) and the first annular disc (21) oscillate in anticlockwise direction relative to the axis (X).

Evidently, when the maneuvering lever (20) and the first annular disc (21) oscillate in clockwise direction relative to the axis (X), said pegs (32) do not receive the driving action of the first annular disc (21), simply sliding inside and along said curved slots (22), without hindering the free rotation of the first annular disc (21) in clockwise direction.

In order to determine and maintain a correct position of the first annular disc (21) and of the second annular disc (30) relative to the housing (1) until the maneuvering lever (20) is in idle position, precompressed springs are provided to make the two annular discs (21 and 30) occupy and maintain their correct position.

Of course, in order to drive said maneuvering lever (20) in inverse oscillations, it is necessary to overcome the antagonist resistance of said springs, which practically act as return springs of the maneuvering lever towards its idle position.

Moreover, the springs are used to adjust the force that is necessary to operate the control, thus adjusting the lever sensitivity. Considering that, according to the user's disability, the control may be operated by pushing with the entire arm, the control sensitivity must be appropriate to the user's capability to modulate his or her force.

Figure 5:
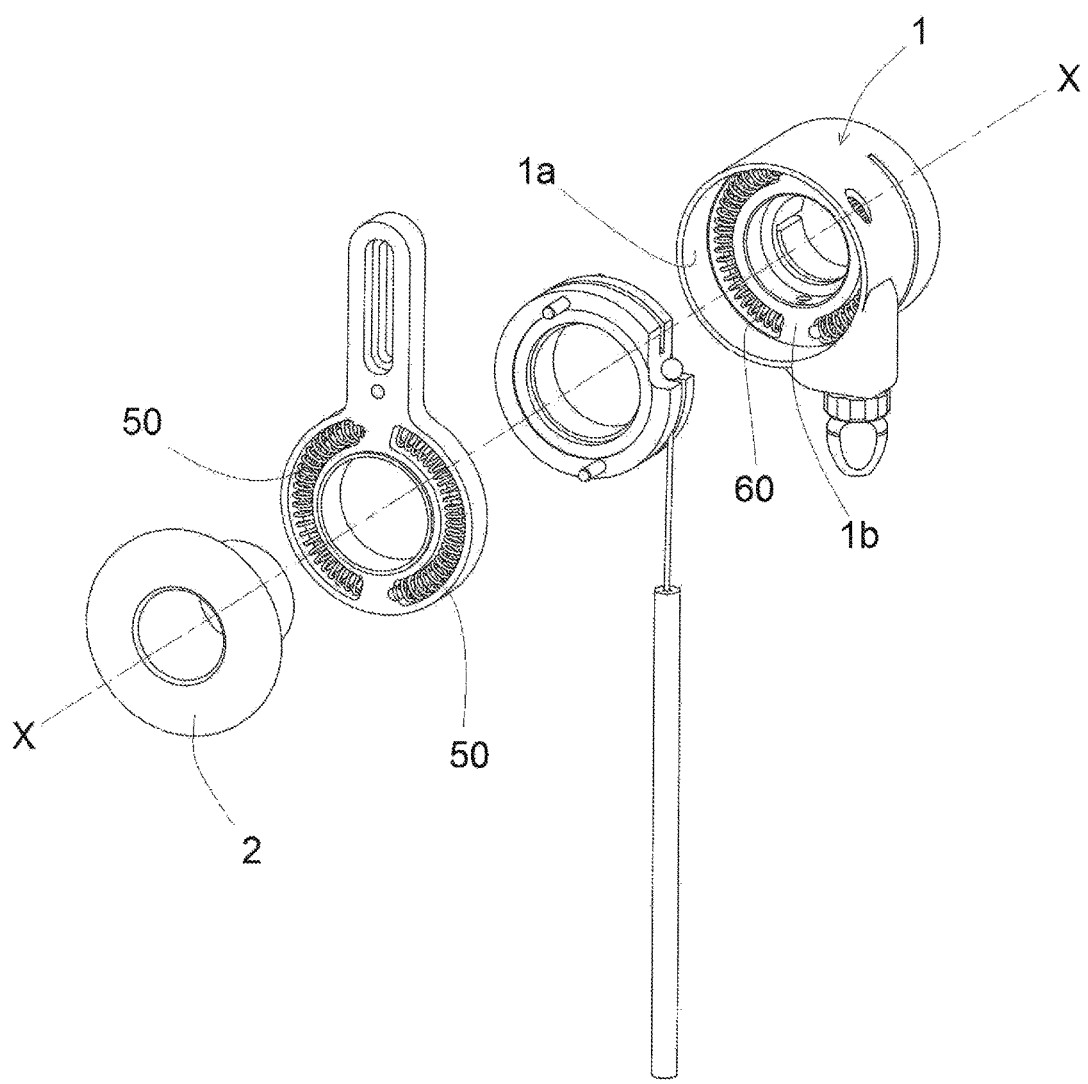
FIG. 5 is the same as FIG. 2, except for the addition of some structural parts that are omitted in FIG. 2 for purposes of graphic clarity.
Figure 6:
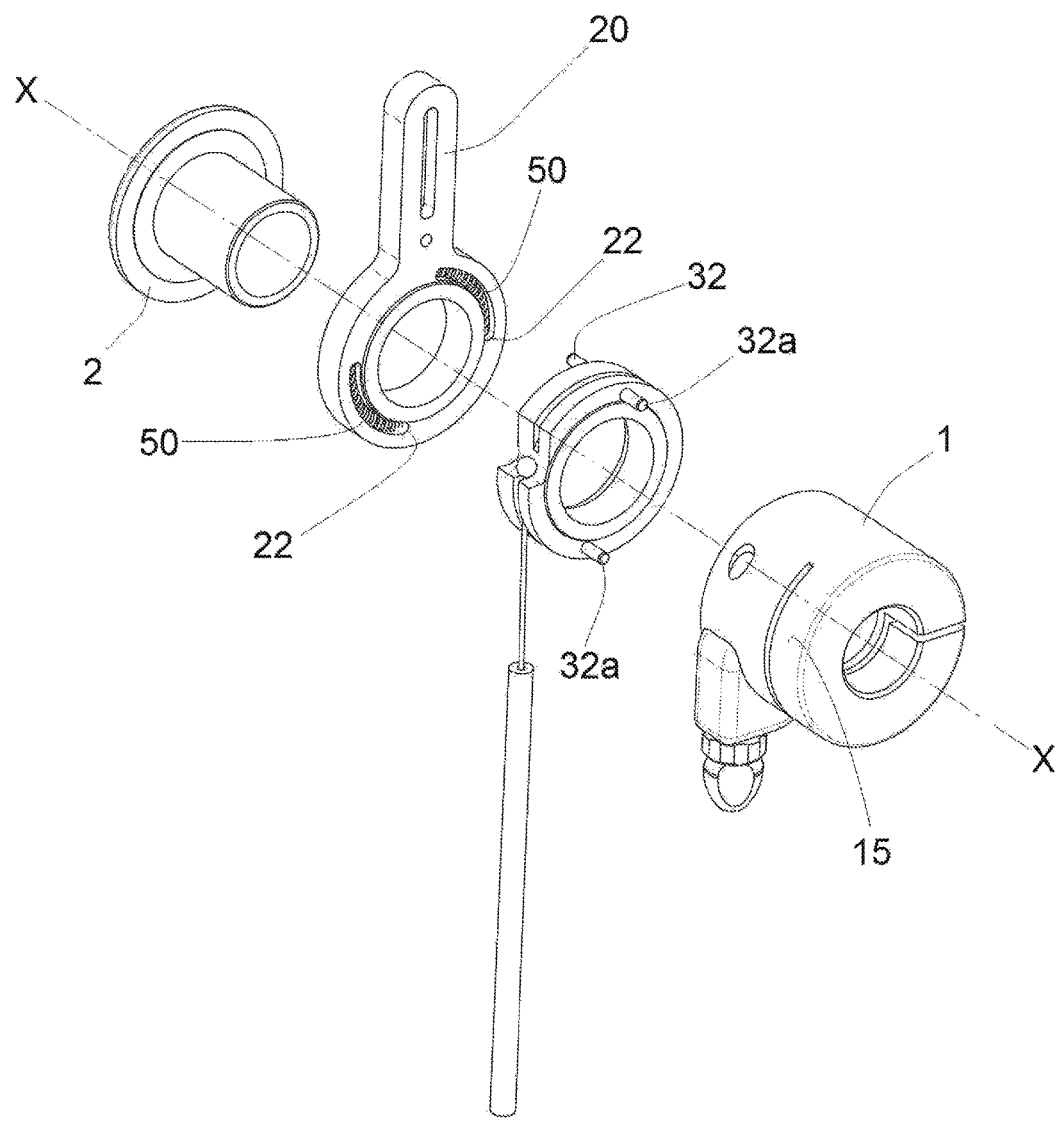
FIG. 6 is a view of all the parts shown in FIG. 5, seen from an opposite angle of 180°.

To better understand the position and the operation mode of said springs, reference is made to FIGS. 5 and 6.

With reference to FIG. 5, it must be noted that, on the side facing the cap (2), the first annular disc (21) is provided with a diametrally opposite pair of curved grooves (23), on the bottom walls (23*a*) of which said curved slots (22) are obtained.

Precompressed springs (50) are situated inside said curved grooves (23), constantly pressing against the pegs (32).

Said springs (50) are compressed by the pegs (32) only when the pegs (32) slide along the slots (22), i.e. when the maneuvering lever (20) is pushed in clockwise direction (as indicated by the arrow F1).

With reference to FIG. 6, it must be noted that, on the side facing the housing (1), the second annular disc (30) is provided with a diametrally opposite pair of counter-pegs (32*a*) that are coaxial with the pegs (32) obtained on the other side of the second annular disc (30).

With reference to FIG. 2, it must be noted that the cylindrical chamber (1*a*) obtained inside the housing (1) is provided on the bottom wall (1*b*) with a diametrally opposite pair of curved grooves (10) where precompressed springs (60), which are only shown in FIG. 5, are situated, constantly pressing against the counter-pegs (32*a*) and keeping them stopped against one (10*a*) of the ends of said curved grooves (10).

Said springs (60) are compressed by the counter-pegs (32*a*) only when the counter-pegs (32*a*) are driven into rotation with the second annular disc (30), i.e. only when the maneuvering lever (20) is pushed in anticlockwise direction (as indicated by the arrow F2), said direction corresponding to a progressive sliding of said counter-pegs (32*a*) along and inside said curved grooves (10). On the other hand, the second annular disc (30) cannot rotate in clockwise direction (as indicated by the arrow F1) relative to the housing (1) because of the interference between said counter-pegs (32*a*) with one (10*a*) of the ends of said curved grooves (10).

The oscillations of the first (21) and of the second (30) annular disc around the axis (X) are guided by a shaft (2*a*) whereon both annular discs (21 and 30) are exactly inserted, being free to idle.

Figure 4:
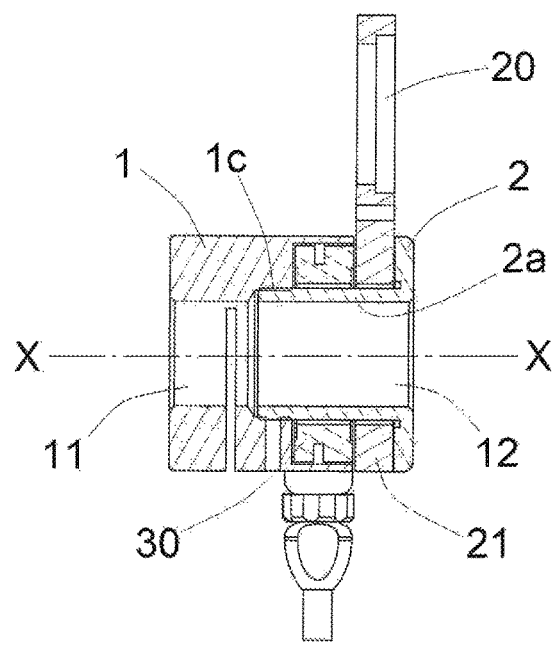
FIG. 4 is the section of FIG. 3 with the section plane IV shown in FIG. 3.

Said shaft (2*a*) is obtained on the cap (2) that closes the housing (1), as shown in FIG. 4, which also shows that the end of said shaft (2*a*) finds a centering seat (1*c*) inside the cylindrical chamber (1*a*).

As shown in FIGS. 2 and 6, the second annular disc (30) is provided with a notch (31) for fastening the actuation cable (40) of the braking apparatus of the wheels of the wheelchair. During the rotation of the second annular disk (30), said actuation cable (40) is wound and housed inside an annular groove (33) obtained on the external edge of said annular disc (30).

As mentioned above, the maneuvering lever (20) is suitable for being coupled with the actuation means of the acceleration apparatus of the motor of the wheelchair.

In view of the above, the maneuvering lever (20) is provided with a hole (25) and a slot (26) that can be selectively and indifferently used to fasten cables or suitably shaped appendages to operate the accelerator control means. According to the preferred embodiment of the device (100), the shaft (2a) has a tubular shape and said housing (1) has a through hole (11) that is identical and coaxial to the internal conduit (12) of said tubular shaft (2a).

Such a structural configuration of the housing (1) and of the shaft (2a) favors the mounting of the device (100) on the handlebar of the wheelchair or on a bar with circular section (not shown in the figures) that can be inserted through said hole (11) and conduit (12).

Figure 1A:
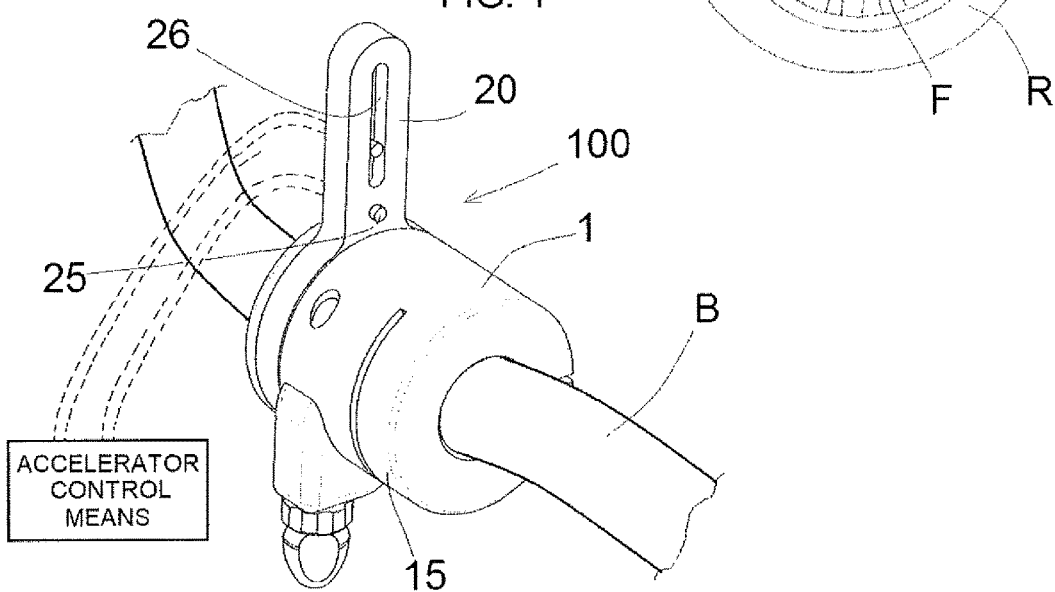
FIG. 1A is an enlarged view of a detail of FIG. 1.

According to the preferred embodiment of the housing (1), the housing (1) ends with a section (15) shaped as an open ring, which is elastically deformed when tightened, used to fasten the device (100) on the handlebar or on the bar inserted through said hole (11) and conduit (12), as shown in FIG. 1A.

As mentioned above, the device (100) can be mounted either on the right end or on the left end of the handlebar of the wheelchair, in order to operate the maneuvering lever (20) with the right hand or with the left hand.

The mounting of the device (100) on either side of the handlebar simply requires to overturn the housing (1) by 180°, consequently inverting the oscillation directions of the maneuvering lever (20) that correspond to the operation of the brake and of the accelerator.

Finally, an additional advantage of the motorized wheelchair according to the invention consists in the fact that it can be also operated by disabled users who have completely lost the movements of both hands, and maintain a satisfactory motor capacity and sensitivity of the forearm, which can be moved forward and backward, as well as turned rightwards or leftwards. In such a case, it will be simply necessary to use a suitably shaped bracket fastened to the wrist of the disabled user on one side, and to the maneuvering lever (20) on the other side.

Finally, although a pair of pegs (32) and a pair of counter-pegs (32a) are used in the preferred embodiment of the invention as described above, respectively receiving the thrust of corresponding pairs of springs (50 and 60), the operation of the control device (100) could be in any case obtained with only one peg (32) and with only one counter-peg (32a), respectively receiving the thrust of only one spring (50) and of only one spring (60). However, the provision of a pair of pegs (32) and of a pair of counter-pegs (32a) is recommended in order to ensure a better balance of the system.

I claim:

1. A motorized wheelchair for disabled or elderly users, the motorized wheelchair comprising;
    a frame;
    a seat adapted for use by a disabled driver;
    a handlebar;
    a motor having an acceleration controller;
    a wheel assembly;
    a brake cooperative with said wheel assembly; and
    a dual-action control device interfaced with said acceleration controller of the motor and with said brake, said dual-action control device comprising:
        a shell-shaped housing having with a cylindrical internal chamber closed by a cap;
        a maneuvering lever movable from an idle position both in a clockwise direction and in a counterclockwise direction relative to a longitudinal axis (X) of said cylindrical internal chamber;
        a first annular disc cooperative said maneuvering lever, said first annular disc having a center on the longitudinal axis (X);
        a second annular disc interfaced with and cooperate with said first annular disc, said second annular disc housed inside said chamber and having a center thereof on the longitudinal axis (X);
        a shaft whereon said first annular disc and said second annular disc are revolvingly mounted; and
        a coupler positioned between said first annular disc and said second annular disc such that said second annular disc is driven into rotation by said first annular disc only in one of the clockwise direction and the counterclockwise direction of the maneuvering lever, said coupler comprising slots on said first annular disc and pegs on said second annular disc.

2. The motorized wheelchair of claim 1, wherein said coupler comprises:
    said slots being a diametrally opposite pair of identical curved slots in said first annular disc;
    said pegs being a diametrally opposite pair of identical cylindrical pegs affixed to said second annular disc on a side facing said first annular disc, said diametrically opposite pair of identical cylindrical pegs having an axis parallel to the longitudinal axis (X) and slidingly received inside respectively said diametrically opposite pair of identical curved slots;
    a diametrally opposite pair of counter-pegs that are coaxial with the diametrically opposite pair of identical cylindrical pegs and positioned on another side of said second annular disc; and
    a diametrally opposite pair of curved grooves formed on a bottom wall of said cylindrical chamber and guiding said diametrically opposite pair of counter-pegs when said second annular disc is driven into rotation by said maneuvering lever.

3. The motorized wheelchair claim 2, further comprising:
    precompressed springs adapted to cause and constantly maintain a position of said first annular disc and said second annular disc relative to said housing, said precompressed springs urging said maneuvering lever to the idle position.

4. The motorized wheelchair of claim 3, wherein said first annular disc has a diametrally opposite pair of curved grooves on a side of said first annular disc facing said cap, said diametrically opposite pair of curved grooves of the first annular disc having bottom walls, said diametrically opposite pair of identical curved slots being on the respective bottom walls of the diametrically opposite pair of curved grooves of the first annular disc.

5. The motorized wheelchair of claim 3, wherein said cylindrical chamber having the diametrally opposite pair of curved grooves formed on the bottom wall of said cylindrical chamber, wherein said precompressed springs are positioned in diametrally opposite pair of curved grooves or the cylindrical chamber.

6. The motorized wheelchair of claim 1, wherein said second annular disc has a notch for fastening an actuation cable of the brake, said actuation cable being wound during a rotation of said second annular disc and housed inside an annular groove on an external edge of said second annular disc.

7. The motorized wheelchair of claim 1, wherein said maneuvering lever has a hole and a slot that fastens cables cooperative with said acceleration controller.

8. The motorized wheelchair of claim 1, wherein said shaft is tubular and said housing has a through hole that is identical and coaxial to an internal conduit of said shaft.

* * * * *